(12) United States Patent
Fabricius (10) Patent No.: US 10,098,906 B2
(45) Date of Patent: Oct. 16, 2018

(54) MODULATION OF THE PHYSICAL INTERACTION BETWEEN PLATELETS AND THE CELL SURFACE EFFECTING CELL PROLIFERATION

(71) Applicant: Cell Receptor GmbH, Genève (CH)

(72) Inventor: Hans-Ake Fabricius, Berlin (DE)

(73) Assignee: CELL RECEPTOR AG, Genéve (CH)

( * ) Notice: Subject to any disclaimer, the term of this patent is extended or adjusted under 35 U.S.C. 154(b) by 44 days.

(21) Appl. No.: 15/031,020

(22) PCT Filed: Oct. 22, 2014

(86) PCT No.: PCT/EP2014/072620
§ 371 (c)(1),
(2) Date: Apr. 21, 2016

(87) PCT Pub. No.: WO2015/059177
PCT Pub. Date: Apr. 30, 2015

(65) Prior Publication Data
US 2016/0367589 A1    Dec. 22, 2016

(30) Foreign Application Priority Data
Oct. 22, 2013    (DE) ........................ 10 2013 111 630

(51) Int. Cl.
| A61K 31/737 | (2006.01) |
| A61K 31/727 | (2006.01) |
| C08B 37/02  | (2006.01) |
| C08B 37/00  | (2006.01) |

(52) U.S. Cl.
CPC .......... *A61K 31/727* (2013.01); *A61K 31/737* (2013.01); *C08B 37/0021* (2013.01); *C08B 37/0057* (2013.01); *C08B 37/0063* (2013.01); *C08B 37/0069* (2013.01); *C08B 37/0078* (2013.01); *C08B 37/0084* (2013.01)

(58) Field of Classification Search
None
See application file for complete search history.

(56) References Cited

U.S. PATENT DOCUMENTS

| 8,987,231 | B2 * | 3/2015 | Viscomi | ............... A61K 31/737 514/54 |
| 9,737,614 | B2 * | 8/2017 | Heller | ...................... A61K 9/06 |
| 2006/0172968 | A1 | 8/2006 | Casu et al. | |
| 2015/0111849 | A1 * | 4/2015 | McCrea | ............... A61M 1/3679 514/56 |

FOREIGN PATENT DOCUMENTS

| WO | WO 92/01003 A1 | 1/1992 |
| WO | WO 2006/083328 A2 | 8/2006 |
| WO | WO2010/096466 | * 8/2010 ........... A61K 31/728 |

OTHER PUBLICATIONS

Mousa et al., "Anti-cancer properties of low-molecular-weight heparin: Preclinical evidence" Thromb Haemost 2009; 102: 258-267.*
Kim et al., "Fucoidan present in brown algae induces apoptosis of human colon cancer cells" BMC Gastroenterology 2010, 10:96 pp. 1-11.*
Lecumberri, R. et al. 2013 "Adjuvant therapy with bemiparin in patients with limited-stage small cell lung cancer Results from the ABEL study" Thrombosis Research 132: 666-670.
Sasisekharan, R. et al. 2002 "Roles of heparin-sulphate glycosaminoglycans in cancer" Nature Reviews 2: 521-528.
Varki, A. et al. 2001 "P-selectin, carcinoma metastasis and heparin: novel mechanistic conections with therapeutic implications" Brazilian J Med and Biol Res 34: 711-717.
Nguyen et al. 1993 "Pentosan inhibits antiogenesis in vitro and suppresses prostate tumor growth in vivo" Anticancer Research 13: 2143-2148.
Karussis, D. et al. 1998 "Suppression of Experimental Autoimmune Encephalomyelitis (EAE) with Low Molecular Weight Heparin" Poster Abstract No. 313 Journal of Neuroimmunology 90: 13-105.
Novotny, F. 1985 "Psoriasis Treatment by Heparin" Acta Universitatis Carolinae Medica 31: 243-245.
Ornstein, D.L. and Zacharski, L. R. 1999 "The Use of Heparin for Treating Human Malignancies" Haemostasis 29(Suppl 1): 48-50.
Abu Arab, W. et al. 2011 "Concentration- and time-dependent effects of enoxaparin on human adenocarcinomic epithelial cell line A549 proliferation in vitro" Can J Physiol Pharmacol 89(10): 705-711.
Elit, L.M. et al. 2012 "Dalteparin low molecular weight heparin (LMWH) in ovarian cancer: a phase II randomized study" Thromb Res 130(6): 894-900.
Park, J.-S. et al. 2002 "Increased anticancer activity by the sulfated Fucoidan from Korean Brown Seaweeds" Journal of the Korean Chemical Society 46(2): 151-156.

* cited by examiner

*Primary Examiner* — Eric Olson
(74) *Attorney, Agent, or Firm* — Knobbe, Martens, Olson & Bear, LLP

(57) ABSTRACT

The growth and/or proliferation of mammalian cells are modulated by modulating the physical interaction between platelets (thrombocytes) and the surface of the cells. Sulfated polysaccharides, preferably glycosaminoglycans, can be used as a medicament for the inhibition of the physical interaction between the cell surface and platelets in the treatment of a medical disorder associated with unwanted cell growth and/or proliferation. The physical interaction between platelets (thrombocytes) and the surface of the cells can be modulated in vitro in order to modulate cell proliferation. Inhibition of the interaction between the cell surface and platelets can inhibit cell growth, and enhancement of the interaction between platelets and the surface of the cell can enhance cell growth.

10 Claims, 7 Drawing Sheets

MODULATION OF THE PHYSICAL INTERACTION BETWEEN PLATELETS AND THE CELL SURFACE EFFECTING CELL PROLIFERATION

The invention relates to a method for modulating the growth and/or proliferation of mammalian cells by modulating the physical interaction between platelets (thrombocytes) and the surface of the cells. The invention therefore relates to sulfated polysaccharides, preferably glycosaminoglycans, for use as a medicament for the inhibition of the physical interaction between the cell surface and platelets in the treatment of a medical disorder associated with unwanted cell growth and/or proliferation. In vitro methods for modulating the physical interaction between platelets (thrombocytes) and the surface of the cells in order to modulate cell proliferation are also encompassed by the invention. The invention therefore relates to the inhibition of the interaction between the cell surface and platelets for the inhibition of cell growth, and an enhancement of the interaction between platelets and the surface of the cell in order to enhance cell growth.

BACKGROUND OF THE INVENTION

Most human primary and permanent cell lines grown in vitro require the presence of serum, either human or of other animal origin, for stable cell growth and proliferation. Serum is the supernatant produced by clotting of blood and spinning off the sediment. Attempts to culture serum-dependent cell lines in culture media, in which serum is substituted with chemical additives or with platelet-free plasma, usually fail. In contrast, platelet lysate can in some culture systems be used to support cell proliferation. This is in part due to the presence of platelet derived growth factors (PDGF), which are released during platelet activation that occurs during blood clotting. This provides the growth-promoting serum with its proliferation-stimulating properties, which are essential for the proliferation and growth of the majority of mammalian cell lines in vitro.

It can be assumed that cells in vivo have a similar dependence on PDGF, as cells in vitro. However, serum is not present in blood circulation in vivo. It is not compatible with the physiological requirements for survival of higher organisms. Growth factors are consequently present in vivo in the blood not as free substances, rather in vesicles within platelets. PDGF is however released from platelets upon activation.

As growth factors are essential for the growth of normal and malignant cells, they must be made available to the cells. Cells that have left the G0 phase and are poised in the G1 phase, require appropriate signals regarding entry into S phase and associated cell proliferation. Therefore, activation of platelets, resulting in the release of growth factors, is an important mechanism inherent in the initiation of cell proliferation and cell growth in vivo. Another aspect of this mechanism is the topology. The growth factors have to be released from the platelets at the site where they are needed. The platelet activation must take place exactly at the site of the cells committed to growth. The mechanism accomplishing this has until now not been subject to in depth investigation.

It is known in the art that platelets bind to the surface of some tumor cells and that this binding is involved in tumor metastasis. For example, Modery-Pawlowski et al. (Biomacromolecules 2013, 14, 910-919) and Takagi et al. (PLOS ONE, August 2013, 8, 8, e73609) disclose that a physical interaction between platelets and tumor cells can play an important role in the metastasis of these cells.

In some tumor cells, platelet receptors are overexpressed, resulting in enhanced platelet aggregation to the surface of tumor cells. Although the studies described previously disclose a correlation between platelet-cell surface-binding with the metastasis of the cells, a relationship between cell growth, in particular tumor cell proliferation, and a physical interaction of platelets on the cell surface has not been described.

Suppression of cell proliferation plays a central role in the treatment of diseases associated with undesired cell growth. Physicians and manufacturers of pharmaceutical products have attempted for decades to develop effective strategies to inhibit undesired cell proliferation of a tumor. The provision of PDGF to tumor cells via an interaction with platelets can be considered as an important target to inhibit the growth or proliferation of tumor cells.

Glycosaminoglycans comprise a linear structure of repeating disaccharides. Heparin is one example of the glycosaminoglycans. Heparin is an endogenous polysaccharide, which has an inhibitory effect on the coagulation cascade and is therefore used therapeutically for anticoagulation. Heparin is known not only as an anticoagulant, but also as a potential therapeutic agent for the prevention of tumor metastasis. The use of heparin for the inhibition of tumor cell metastasis has been described in the art (Ma et al, Invest New Drugs (2012) 30: 508). The use of low molecular weight heparin resulted in reduced metastasis of colon tumors. Activity against cell growth or cell proliferation of tumors after administration of low molecular weight heparin was not identified by the authors of this study.

SUMMARY OF THE INVENTION

In light of the prior art the technical problem underlying the present invention is to provide means for modulating cell proliferation.

This problem is solved by the features of the independent claims. Preferred embodiments of the present invention are provided by the dependent claims.

Proliferating cells, normal cells of various degrees of differentiation and malignant cells have a common and surprisingly basic property, which is not present in resting cells: They are able to bind platelets. Platelets contain—among other substances—growth factors, which are able to sustain cell growth. Depletion of platelet derived growth factors results in halting cell growth and eventually leading to cell death (apoptosis). The present application provides a group of substances, which are able to interfere with the binding of platelets to proliferating cells and are therefore able to interfere with cell growth and subsequently provide a therapeutic effect.

The invention therefore relates to a method for modulating the proliferation of mammalian cells by blocking the physical interaction between platelets (thrombocytes) and the surface of said cells.

The realization that the physical interaction between platelets and the surface of a cell is necessary for cell proliferation both in vivo and in vitro represents a new and surprising feature of the invention. Although the interaction between platelets and the surface of a tumor cell may play a role in the metastasis of tumor cells, it has not been described previously in the prior art that the interaction influences cell proliferation directly through physical interaction.

In one embodiment the invention relates to a method as described herein, wherein inhibition of the physical interaction between the cell surface and platelets inhibits cell growth and/or proliferation.

In one embodiment the invention relates to a method as described herein, wherein said proliferating cells are human cells.

In a preferred embodiment the invention relates to a sulfated polysaccharide for use as a medicament for the inhibition of the physical interaction between the cell surface and platelets in the treatment of a medical disorder associated with unwanted cell growth and/or proliferation.

Surprisingly, a sulfated polysaccharide, such as a glycosaminoglycan, such as heparin, or other low molecular weight glycan molecule, such as a LMW heparin or other LMW glycosaminoglycan, or a sulfated alginate, may be administered to inhibit the binding between the cell surface and platelets. This disturbance in the physical interaction causes the cells to be inhibited in their proliferation. It has not been disclosed in the prior art that the application of sulfated polysaccharides can cause inhibition of cell proliferation via the disruption of the interaction between the cell surface and platelets. Such sulfated polysaccharides may be referred to as "inhibitors" according to the present invention.

Inhibition of cell proliferation due to prevention of platelet-cell surface interaction by the administration of sulfated polysaccharide represents a novel technical effect. Due to this technical effect one or more novel clinical situations arise.

Previously, only the metastatic seeding of tumor cells was considered to be preventable or treatable with heparin. The present invention enables a novel application of sulfated polysaccharides for the inhibition of cell proliferation, which is an underlying prerequisite for tumor metastasis. According to the present invention, patients with tumors, regardless of whether metastasis has occurred or not, may be treated with sulfated polysaccharides with the intention of utilizing the novel technical effect of disrupting the platelet-cell surface interaction and subsequent effects on cell growth and/or proliferation even before metastasis has occurred.

In one embodiment the invention relates to a method as described herein, wherein the physical interaction between platelets and the cell surface is mediated by a platelet receptor located on the surface of the cells. Because physiological cell growth in vivo is subject to control systems dependent on platelet receptors, the receptors play an important role cell proliferation regulation. Platelet receptors typically are present on the cell surface with the passage of cells from the G0-phase in the cell cycle on the surface of proliferating cells. The modulation of this process provides effective means to modulate cell growth.

Through experimental approaches such as those described below, the inventors have identified the surprising feature that sulfation of polysaccharides, such as glycosaminoglycans, leads to an enhanced disruption of the platelet-cell surface interaction. Varying degrees of sulfation occur in both naturally occurring and synthetic sulfated polysaccharides. In a preferred embodiment the sulfated polysaccharides may be selected, or modified, for particular degrees of sulfation in order to enhance the technical effect described herein.

Sulfation causes a molecule to become negatively charged. Heparin is the most negatively charged organic molecule occurring in living organisms. Higher sulfated polysaccharides, such as glycosaminoglycans, and hence more negatively charged sulfated polysaccharides, are more effective in inhibiting the platelet-cell interaction than lower sulfated, and hence less negatively charged, sulfated polysaccharides.

A negative charge of the inhibitor is a determining feature of the mechanism underlying the inhibition of the platelet-cell binding mentioned above. It is reasonable to conclude that the cell membrane, most probably of those cells committed to proliferation, possesses structures resembling sulfated glycosaminoglycans, which are able to bind platelets. The inhibitor of the platelet-cell surface interaction of the present invention then acts competitively, in that it blocks another membrane receptor molecule, now most probably on the platelet, which is normally responsible for recognizing the negatively charged molecule on the membrane of the cell committed to proliferation. A higher sulfated polysaccharide is thus able to block several such receptor molecules at once and will have a higher chance of being bound before it is diluted or washed away with body fluids.

The degree of sulfation of the sulfated polysaccharide may be preferably about 0.5, 0.6, 0.7, 0.8, 0.9, 1.0, 1.1, 1.2, 1.3, 1.4, 1.5, 1.6, 1.7, 1.8, 1.9, 2.0, or more than 2.0. In a preferred embodiment the invention relates to a sulfated polysaccharide for use as a medicament as described herein, wherein the degree of sulfation of the polysaccharide is ≥1.0.

In a preferred embodiment the invention relates to a sulfated polysaccharide for use as a medicament as described herein, wherein the degree of sulfation of the polysaccharide is ≥1.2.

In a preferred embodiment the invention relates to a sulfated polysaccharide for use as a medicament as described herein, wherein the degree of sulfation of the polysaccharide is ≥1.4.

As described below, the degree of sulfation of any given polysaccharide can be adjusted using methods known to those skilled in the art. The degree of sulfation can also be determined with appropriate experimentation, thereby enabling a skilled person to adjust the degree of sulfation in order to produce a polysaccharide that exhibits optimal properties for the intended use. Commercially available or naturally obtained polysaccharide molecules could therefore be modified to adjust the respective degree of sulfation accordingly.

In one embodiment of the invention the sulfated polysaccharide for use as a medicament as described herein is a glycosaminoglycan.

In one embodiment of the invention the glycosaminoglycan for use as a medicament as described herein is heparin. Heparin has been applied in tumor therapy previously, although no effect has been shown on the platelet-cell surface interaction. The novel technical effect of disturbing platelet binding enables a novel medical use of heparin, in particular for targeting those medical conditions in which a reduction of cell proliferation and/or cell growth is required.

Glycosaminoglycan molecules with a degree of sulfation above 1.0 are typically heparin, and other sulfated low molecular weight (LMW) variants of heparin, in addition to other glycosaminoglycan molecules such as pentosan polysulfate (PPS) or dextran sulfate (DXS).

In one embodiment of the invention the glycosaminoglycan for use as a medicament as described herein is a low molecular weight (LMW) heparin.

In one embodiment the invention relates to LMW heparin for use as a medicament as described herein, wherein the low molecular weight heparin is enoxaparin.

In one embodiment the invention relates to LMW heparin for use as a medicament as described herein, wherein the low molecular weight heparin is dalteparin.

In one embodiment the invention relates to LMW heparin for use as a medicament as described herein, wherein the low molecular weight heparin is tinzaparin.

In a preferred embodiment the invention relates to a glycosaminoglycan for use as a medicament as described herein, wherein the glycosaminoglycan is characterised by the absence of the terminal pentasaccharide of Heparin, preferably the absence of the pentasaccharide GlcNAc/NS (6S)-GlcA-GlcNS(3S,6S)-IdoA(2S)-GlcNS(6S).

In a preferred embodiment the invention therefore relates to a glycosaminoglycan for use as a medicament as described herein, wherein the glycosaminoglycan is pentosan polysulfate (PPS).

In a preferred embodiment the invention therefore relates to a glycosaminoglycan for use as a medicament as described herein, wherein the glycosaminoglycan is dextran sulfate (DXS).

In a preferred embodiment of the invention the glycosaminoglycan characterised by the absence of the terminal pentasaccharide of Heparin, preferably exhibits a molecular weight of 1000 to about 500 000 daltons, preferably 2000 to 100 000 daltons, more preferably from about 5000 to about 12 000 daltons, or essentially the same approximate molecular weight as the low molecular weight heparin molecules disclosed herein. Glycosaminoglycans from about 5000 to about 12000 daltons molecular may be termed low molecular weight glycosaminoglycans.

In one embodiment the glycosaminoglycan characterised by the absence of the terminal pentasaccharide of Heparin, such as DXS or PPS, has a molecular weight of from about 2 kDa to about 12 kDa, more preferably about 3 kDa to about 8 kDa, most preferably of about 4 kDa to about 6 kDa. The low molecular weight glycosaminoglycans as described herein (about 2 kDa to about 12 kDa, preferably under 8 kDa) are characterised by additional advantages in comparison to unfractionated or high molecular weight glycosaminoglycans. The low molecular weight glycosaminoglycans typically lead to lower amounts of platelet aggregates than unfractionated or high molecular weight preparations. Through the administration of such relatively low molecular weight preparations the complication of a thrombosis during treatment is significantly reduced.

In a surprising fashion, the glycosaminoglycans characterised by the absence of the terminal pentasaccharide of Heparin, in addition to other sulfated polysaccharides characterised by the absence of the terminal pentasaccharide of Heparin such as alginates, enable reduced risk of both thrombocytopenia (potentially caused by excessive blood thinning) and thrombosis (unwanted clotting). Although these two complications appear to be due to contrasting mechanisms, either may occur during treatment with unfractionated glycosaminoglycans, such as unfractionated heparin. Unfractionated heparin can therefore reduce platelet numbers too strongly, or can lead to platelet aggregation, either of which may lead to dangerous side effects. Surprisingly, PPS and DXS both show beneficial properties that enable the avoidance of these effects. In vitro studies have shown reduced platelet aggregation is caused by DXS and PPS (in comparison to UFH) in addition to reduced anticoagulation.

The DXS used in the experimental examples is obtained from Sigma (31404; Dextran sulfate sodium salt from Leuconostoc spec), with an average MW of 5000 daltons. A similar or the same average molecular weight maybe used for PPS. The present examples utilise SP 54 (sodium salt) as PPS.

In one embodiment, the molecular weight of the relevant glycosaminoglycan can be determined using mass spectrometry based method, such as is described in Rhomberg et al (PNAS, vol. 95 no. 8, 4176-4181). The particular saccharide structure and further information on sulfation and molecular weight can be determined using sequencing techniques disclosed in Turnbull et al (PNAS, vol. 96 no. 6, 2698-2703).

In a preferred embodiment the invention therefore relates to a sulfated polysaccharide for use as a medicament as described herein, wherein the sulfated polysaccharide is a sulfated alginate.

Alginates are unbranched polysaccharides which are produced by algae but also by some bacteria. Alginate is typically present as a gel-forming polysaccharide, which can be found in the cell wall of brown algae.

In a preferred embodiment the invention therefore relates to a sulfated polysaccharide for use as a medicament as described herein, wherein the sulfated polysaccharide is a fucoidan.

Fucoidans are structurally related to alginates. The fucoidans have a natural variable degree of sulfation. This may be modified using methods similar to those applicable for alginates. The sulfation degree of fucoidans may be adjusted accordingly. Both sulfated alginates and sulfated fucoidans have an inhibitory effect on platelet-cell binding.

Heparin has two ways of acting as an anticoagulant, namely by inhibition of the clotting factor Xa and inhibition of Thrombin. Unfractionated heparin (UFH) does frequently, however, cause severe thrombocytopenia. The primary mechanism of heparin is the inhibition of the clotting factor Xa. It is caused by a terminal pentasaccharide sequence at the non-reducing end of the Heparin (GlcNAc/NS(6S)-GlcA-GlcNS(3S,6S)-IdoA(2S)-GlcNS(6S),
Molecular weight 1.7 KD). This pentasaccharide can be produced semisynthetically in a pure form and is as such known under the name of Fondaparinux.

Fondaparinux binds to platelets to a reduced extent compared to heparin and consequently has the lowest rate of thrombocytopenic or thrombotic complications of all preparations mentioned above. Fondaparinux has by the inventors been shown to be relatively poor in inhibiting platelets from binding to growing cells.

The Fondaparinux pentasaccharide is however not contained in either dextran sulfate or pentosan polysulfate, which both exhibit the desired properties regarding platelet-cell surface interaction disruption. Both PPS and DXS possess anti-coagulation properties, which are however much weaker than those of Heparin preparations.

In a preferred embodiment the invention therefore makes technical utilization of the various properties of glycosaminoglycan molecules, by providing glycosaminoglycan variants that show the desired disruption in platelet-cell surface interaction without unwanted side effects associated with blood-thinning or anticoagulant activity, such as thrombocytopenic complications.

Heparin or heparin derivatives exhibit the desired effect (disruption in platelet-cell surface interaction), although in a preferred embodiment those glycosaminoglycan molecules are preferred, that do not comprise the terminal pentasaccharide of Heparin, in order to avoid unwanted anticoagulant side effects.

The technical effect of the present invention is distinct from the known anticoagulant properties of glycosaminoglycan molecules. The present invention relates to a novel technical effect and enables the novel medical use of known compounds. For example, patients at risk of anticoagulant-associated side effects would not previously have been treatable with heparin. For example tumor patients, who may have been treated with heparin or derivatives thereof, with an enhanced risk of anticoagulant-associated side effects, would not previously have been treatable. Due to the utilization of the novel technical effect described herein the treatment of a new patient group has been enabled, namely those with cell proliferation disorders and an enhanced risk of anticoagulant-associated side effects. For example patients with heparin induced thrombocytopenia may be treatable for cell proliferation disorders. In a preferred embodiment glycosaminoglycan molecules characterised by the absence of the terminal pentasaccharide of heparin are intended for administration in these groups, for example PPS and DXS.

Common situations in which heparin is administered, is during either long-term or short-term anticoagulant therapy. Heparin typically acts faster and more directly than coumarine derivatives, which are used for long-term treatment. Heparin is typically preferred for treatment initiation or for a short-term treatment. Concrete examples of heparin treatment in the early phases of a long-term treatment include treatment of thrombosis, such as deep vein thrombosis, pulmonary embolism, thrombosis, which has caused a stroke or a heart attack. An example of short-term therapy with heparin is the frequent use of heparin for the prevention of thrombosis in surgical procedures. Patients undergoing such procedures may however be at risk of heparin induced thrombocytopenia, and such patients who also suffer from a disorder associated with unwanted cell proliferation could be effectively treated using the glycosaminoglycan molecules characterised by another saccharide backbone than that of heparin, potentially in combination with Fondaparinux.

In one aspect the invention relates to a sulfated polysaccharide, preferably a glycosaminoglycan, sulfated alginate or fucoidan, for use as a medicament as described herein, wherein the medical disorder associated with unwanted cell growth and/or proliferation is a tumor disease.

In one aspect the invention relates to a sulfated polysaccharide, preferably a glycosaminoglycan, sulfated alginate or fucoidan, for use as a medicament as described herein, wherein the medical disorder associated with unwanted cell growth and/or proliferation is an autoimmune disease.

The pathogenesis of many diseases is associated with cell growth. As an example, an unwanted immune response is one such disease. An immune response leads to proliferation of one or a few concerned cell clones by the immune system in order to produce further immune cells or antibodies to the causative agent. In cases of unwanted or pathogenic immune responses, the effector cells of the immune system, or antibodies produced by the immune system, may be directed against the body's own tissues, leading to autoimmunity. These immune reactions lead to significant tissue damage. This damage causes the disease symptoms of the autoimmune disease.

The proliferation of immune cells may therefore also be influenced pharmacologically in the clinical application of inhibitors of platelet binding to the cell surface. Thus, it is possible to control unwanted activities of the immune system through this mechanism. For this purpose, other drugs currently used tend to have significant side effects. The use of glycosaminoglycans as described herein typically have relatively low side effects and represent a safe way to treat such diseases.

In light of the novel technical effect identified by the inventor, a number of novel clinical situations arise. Until now, a potential anti-metastatic effect of heparin was considered to be due systemic effects related to anti-coagulation. The present invention therefore relates to an entirely novel mechanism, previously unconsidered by the medical community.

Due to the physical interaction between platelets and proliferating cells, in addition to the knowledge that the sulfated polysaccharides directly inhibit cell surface contacts with platelets, the invention may be characterised by the local administration of said sulfated polysaccharide to regions in proximity to tumor tissues. The local administration of sulfated polysaccharide to regions in proximity to tumor tissue enables lower doses of sulfated polysaccharide to be administered, that maintain an effective anti-proliferation effect with reduced systemic toxicity. In the meaning of the present invention, local administration relates to administration, for example via injection, transmucosal or transdermal approaches, to a region within preferably 10 cm, within 5 cm, or preferably within 1 cm to tumor tissue, or delivery within the tumor itself.

Methods of local administration may therefore relate to parenteral administration, such as intravenous (into a vein), intra-arterial (into an artery), intraosseous infusion (into the bone marrow), intra-muscular, intracerebral (into the brain parenchyma), intracerebroventricular (into cerebral ventricular system), intrathecal (an injection into the spinal canal) or subcutaneous (under the skin) administration.

In one embodiment local administration relates to intra-arterial administration into an artery responsible for providing blood to a tumor. Such an approach may be particularly relevant in cases where a particular organ or tissue may not be removed from the patient, even in cases where a tumor has developed. The local administration in this region via intra-arterial administration thereby provides a unique method of disrupting interaction between platelets and the cell surface of dividing cells, thereby providing a useful therapeutic effect.

In a further aspect the invention relates to a pharmaceutical composition for the inhibition of the physical interaction between the cell surface and platelets in the treatment of a medical disorder associated with unwanted cell growth and/or proliferation comprising a sulfated polysaccharide as described herein and a pharmaceutically acceptable carrier.

The invention also relates to an in vitro method for inhibiting cell growth and/or proliferation by inhibiting the physical interaction between the cell surface and platelets by in vitro administration of sulfated polysaccharide. The invention therefore relates to the in vitro use of sulfated polysaccharide as described herein in a method of the invention for the inhibition of the physical interaction between the cell surface and platelets. The invention also relates to the in vitro use of sulfated polysaccharide as described herein in a method of the invention for inhibition of cell growth and/or proliferation.

In one embodiment the in vitro use of sulfated polysaccharide in a method of the invention is characterised in that said sulfated polysaccharide is heparin or LMW heparin and is administered in vitro at 0.01 to 10 U/mL, preferably 0.05 to 1, preferably 0.05 to 0.5, more preferably about 0.1 U/mL.

In one embodiment the in vitro use of sulfated polysaccharide in a method of the invention is characterised in that said sulfated polysaccharide is DXS or PPS and is administered in vitro at 0.01 to 10 ppm in solution, preferably 0.05 to 5, more preferably about 1 ppm.

The interaction between platelets and the surface of a cell can not only be inhibited by the use of sulfated polysaccharide, but also be enhanced by the addition of platelets. The invention therefore relates, in another aspect, to a method for modulating cell proliferation, wherein said proliferation is enhanced by increasing physical interaction between platelets and the cell surface. The invention provides a method wherein enhanced interaction between platelets and the surface of the cell enhances cell growth and/or proliferation. Enhancement may relate to a relative measure of cell growth, wherein the control cells would be those treated without or with a reduced amount of the corresponding dose of platelets.

The invention therefore relates to platelets for use as a medicament for the enhancement of the physical interaction between the cell surface and platelets in the treatment of a medical disorder, for which enhanced cell growth and/or proliferation is beneficial in treating said disorder.

In one embodiment the invention relates to platelets for use as a medicament as described herein, wherein the medical disorder, for which enhanced cell growth and/or proliferation is beneficial in treating said disorder, is a wound, such as caused by a traumatic effect or wound healing disturbance following surgery, a disorder which may be accompanied by thrombocytopenia.

The invention therefore also relates to an in vitro method for enhancing cell growth and/or proliferation by enhancing the physical interaction between the cell surface and platelets by in vitro administration of platelets. The in vitro use of platelets in a method of the invention is intended for the enhancement of the physical interaction between the cell surface and platelets. The in vitro method or use as described herein may be characterised in that the platelets are partially activated platelets.

One therapeutic application of the invention is the treatment of wound healing. Chronic diseases such as diabetes, chronic infections such as hepatitis or AIDS are at times associated with impaired wound healing. This can be caused by poor blood supply due to damaged blood vessels, by thrombocytopenia or other disease-related changes in cell membranes. The availability of platelets, which is a prerequisite for coherent cell growth in the healing of the wound edges, may be a problem limiting cell proliferation where platelets cannot reach the edges of the wound in sufficient quantity. A targeted platelet transfusion is therefore encompassed within the invention.

DETAILED DESCRIPTION OF THE INVENTION

The invention relates to the finding that the binding of platelets to cells is associated with cell growth and/or proliferation. Platelets bind those cells present in the cell growth cycle. The medicament-mediated modification of platelet binding to the surface of growing cells can influence cell growth, preferably in vivo but also in vitro.

The invention may be applied in any given scenario where either malignant cancerous or any other uncontrolled growth of cells is present. The invention may also be applied in any medical condition in which nascent, either controlled or uncontrolled cell growth, plays a functional role in the medical indication. Examples include: clonal expansion of effector cells in either a normal or pathological immune response, such as cell growth of pathological immune cells in the intestinal mucosa causing terminal ileitis (Crohn's disease), or regeneration of cells and organs, for example in the bone marrow after bone marrow depression.

Pharmacological modifications of the interaction described herein are provided by the present invention. Suitable materials for the modulation described herein are those that either bind to the surfaces of platelets or to the surfaces of cells poised for cell division, and subsequently lead to a modulation of the cell surface-platelet interaction.

Compounds of particular interest are those known to be associated with the outer cell membrane, such as those belonging to the so-called cell surface glycans. These are often bound to a protein scaffold and thereby form a glycoprotein.

In connection with the present invention, the terms "cell growth" and "proliferation" are both used, and may be used interchangeably. In medicine, especially in oncology, the term cell growth is frequently used with respect to the increase in cell number (eg. due to tumor growth). Tumor growth is caused by increased proliferation of tumor cells. Cell growth, on a scale and increase in volume of a single cell is, under also included within this definition. In a preferred embodiment, the invention relates to modulation of cell proliferation. Cell growth or cell proliferation can be distinguished from the metastasis of tumor cells, which relates to the migration (change in location) of cells. Metastasis and proliferation represent different aspects of a tumor and can be viewed as different clinical indications.

The term "physical interaction between platelets (thrombocytes) and the surface of said cells" relates to any given physical interaction or binding between platelets and the cell surface of greater frequency or strength than would occur by chance when said platelets and cells are present together in vitro. In a preferred embodiment said interaction can be defined and interrogated via carrying out the methods described herein, such as co-culture or incubation, washing (preferably 2 to 4 times) and subsequent fixing and identification.

The term "glycosaminoglycan", as used herein, refers to an oligo- or polysaccharide, comprising preferably aminohexose units. Sulfated glycosaminoglycans include, but are not limited to, chondroitin sulfate, dermatan sulfate, keratan sulfate, heparin, heparan sulfate, pentosan polysulfate (PPS) and dextran polysulfate (DXS).

The term "heparin" includes unfractionated heparin and heparins having a lower molecular weight. In one embodiment, the heparin used in accordance with this invention is "unfractionated heparin" (UFH) which may have an average molecular weight of about 8 kDa to about 30 kDa, preferably of about 10 kDa to about 20 kDa, most preferably of about 12 kDa to about 16 kDa, e.g. about 15 kDa.

The term "heparin" includes also small molecular weight fragments of heparin molecules, either derived from naturally occurring heparin by cleavage and isolation or by synthetic routes.

In another embodiment, the heparin used in accordance with this invention is a low molecular weight heparin (LMWH). LMWHs are heparins or heparin salts having an average molecular weight of less than 8000 Da and for which at least 60% of all chains have a molecular weight less than 8000 Da. Low molecular weight heparin is a term commonly accepted in the art and requires no further clarification for a skilled person. LMWH do not cause thrombocytopenia as frequently as UFH. Their ability to bind platelets is substantially reduced.

Preferably, the molecular weight of the LMWH used in accordance with this invention is about 2 kDa to about 8 kDa, more preferably about 3 kDa to about 6 kDa, most preferably of about 4 kDa to about 5 kDa, e.g. about 4.5 kDa. The LMWHs can be obtained by various methods of fractionation or depolymerisation of polymeric heparin.

Examples of LMWHs include, but are not limited to, ardeparin (Normiflo), certoparin (Sandoparin), enoxaparin (Lovenox and Clexane), parnaparin (Fluxum), tinzaparin (Innohep and Logiparin), dalteparin (Fragmin), reviparin (Clivarin) and nadroparin (Fraxiparin).

Alginate is typically extracted as sodium salt. The monomer units may preferably be a L guluronate (G) and β D mannuronate (M). Polymeric units may comprise homopolymers of G blocks, homopolymers of M blocks and heteroploymers of G/M blocks. Natural alginates generally have no regularly repeating structures that comprise of alternating homopolymeric and heteropolymeric sections, with preferably mannuronic acid and/or guluronic acid. Alginates may function as structural elements or as a protective biofilm.

Sulfation of alginates may be ascertained by FTIR (Fourier-transform infrared spectroscopy), HR-ICP-MS (high resolution mass spectrometry and inductively coupled plasma) and 13C-NMR (NMR, nuclear magnetic resonance) and SEC-MALLS (size-exclusion chromatography with multi-angle laser scattering detection). Alginate molecules may be sulfated via methods known to those skilled in the art, for example by using a sulfating agent such as (N(SO3Na)3), prepared from sodium bisulfate and sodium nitrate in aqueous solution, or chlorsulfonic acid treatment in formamide.

Fucoidan is a sulfated polysaccharide (MW: average 20,000) found mainly in various species of brown algae and brown seaweed such as mozuku, kombu, bladderwrack, wakame, and hijiki. Variant forms of fucoidan have also been found in animal species, including the sea cucumber.

Fucoidan is used as an ingredient in some dietary supplement products. There are at least two known distinct forms of fucoidan: F-fucoidan, which is >95% composed of sulfated esters of fucose, and U-fucoidan, which is approximately 20% glucuronic acid.

As used herein, the term "degree of sulfation" refers to the number of sulfate groups (—OS03) per monosaccharide unit. Although degree of sulfation may be provided in other sources of literature as the number of sulfate groups (—OSO3) per disaccharide unit, the definition of the present invention relates to the number of sulfates per monosaccharide unit. Some GAGs exist not as disachharide polymers but as monosaccharide polymers. In order to provide a consistent degree of sulfation measurement, the degree of sulfation per monosaccharide unit is used and the degrees of sulfation for disaccharide units adjusted accordingly.

Sulfation of any given polysaccharide or GAG may be modified according to the saccharide sulfation methods described in US 20050119469 A1, which is hereby incorporated in its entirety by reference.

The degree of sulfation may be determined by techniques known to those in art, such as those disclosed in Zaia et al (BioMed Research International, Volume 2014 (2014), Article ID 986594) or other related methods using mass spectrometry analysis.

Heparin shows higher degree of sulfation (1-3 sulfates/monosaccharide, preferably 1.5, or 2) when compared to heparan sulfates (0.3-0.7) sulfates/monosaccharide.

TABLE 1

Glycosaminoglycans and sulfation degree (Amended from Wang, Curr Anal Chem. Oct. 1, 2012; 8(4): 506-511).

| GAG | Sugar 1 | Sulfates | Sugar 2 | Sulfates | Degree of Sulfation |
|---|---|---|---|---|---|
| hyaluronan | GlcNAc | none | GlcA | none | 0 |
| chondroitin | GalNAc | none | GlcA | none | 0 |
| chondroitin sulfate | GalNAc | 4S or 6S | GlcA | none | 0.5 |

TABLE 1-continued

Glycosaminoglycans and sulfation degree (Amended from Wang, Curr Anal Chem. Oct. 1, 2012; 8(4): 506-511).

| GAG | Sugar 1 | Sulfates | Sugar 2 | Sulfates | Degree of Sulfation |
|---|---|---|---|---|---|
| dermatan sulfate | GalNAc | 4S | IdoA or GlcA | none | 0.5 |
| heparaosan | GlcNAc | none | GlcA | none | 0 |
| heparan sulfate | GlcNAc or NS | none or 6S or 3S | GlcA | none or 2S | 0.5 |
| heparin | GlcNS or GlcNAc | 6S ± 3S | IdoA or GlcA | 2S | 1.5 |
| N-sulfo heparosan | GlcNS | none | GlcA | none | 0.5 |
| undersulfated heparin | GlcNS or GlcNAc | none or 6S or 3S | GlcA or IdoA | none or 2S | 1 |

The degree of sulfation in Table 1 is the average number of sulfates in the monosaccharide unit of each GAG. Although the GAGs shown are disachharide GAGs, the degree of sulfation has been adjusted for a monosaccharide GAG. Abbreviations are: GlcNAc, N-acetyl-α-D-glucosamine; GalNAc, N-acetyl-β-D-galactosamine; GlcNS, N-sulfo-α-D-glucosamine; GlcA, β-D-glucuronic acid; α-L-IdoA iduronic acid; and S, sulfo.

Pentosan polysulfate (PPS), sold under the name Elmiron, by Ortho-McNeil Pharmaceutical is an oral medication approved by the U.S. Food and Drug Administration (FDA) for the treatment of interstitial cystitis (IC), also known as painful bladder syndrome and under the names of Fibrezym® and Pentosanpolysulfat SP54® by bene Pharma. In the veterinary field, pentosan polysulfate is sold under the name Cartrophen Vet by Biopharm Australia. PPS is also sold under the names Naturevet Equine and Arthropen. The anticoagulant activity of PPS is 1/15 that of Heparin. PPS is a highly sulfated semisynthetic polysaccharide possessing a higher negative charge density and degree of sulfation than heparin. Like other glycosaminoglycans, the structural and chemical properties of PPS promote binding of the drug to the endothelium. PPS typically exhibits a degree of sulfation greater than 1.5 sulfate group per glucosyl residue.

Dextran sulfate (DXS) is a polyanionic derivative of dextran produced by esterification of Dextran with chlorosulphonic acid. DXS is a branched-chain polysaccharide polymer of d-glucose that is permeable to water and forms a viscid gelatinous material. The sulfur content is approximately 17% which corresponds to an average of 1.9 sulfate groups per glucosyl residue of the dextran molecule.

Every normal tissue has one or more endogenous mechanisms of controlling its growth. Tissue can be in a normal state, i.e with in a largely resting state with diploid nuclei only. A growing (proliferating) tissue has additional nuclei with an increased DNA content as a consequence of DNA synthesis which is necessary for cell growth. Such tissue tends to have an increased amount of microscopically visible cell division.

Cell growth is related but not limited to: Growth of organs during embryogenesis, childhood and adolescence or after mechanical or toxic lesions of organs, and to normal or pathological immune response and to cancerous tissues but is also normally present as persistent growth of mucosa, skin cells and bone marrow.

Examples of diseases and disorders resulting from deficient control of growth mechanisms relate to:
  Malignant cell growth, in particular tumor growth,
  Regeneration of tissue such as bone marrow, connective tissue, epithelium, Modulation of the immune response (autoimmune diseases)

According to the present invention "cancer" or "proliferative disorder" as used herein is a group of proliferative diseases or disorders characterized by the uncontrolled growth and/or spread of malignantly altered endogenous cells.

Cancer as used herein may relate to any given carcinoma, such as those arising from ectodermal tissues i.e. cancer of the skin, breast, nervous system and such as those arising from mesodermal tissue i.e. cancer of bone, cartilage, muscle, kidney, lymphoma or leukemia, germ cell tumors, and those arising from endodermal tissues i.e. cancer of the liver, pancreas, thyroid gland, lung, stomach, bowel and bladder, caused by alterations in the growth control mechanisms of the tissues affected.

Examples of cancer include, but are not limited to Hodgkin's disease, non-Hodgkin's lymphoma, acute lymphocytic leukemia, multiple myeloma, neuroblastoma, breast carcinoma, ovarian carcinoma, lung carcinoma, Wilms' tumor, testicular carcinoma, soft-tissue sarcoma, bladder carcinoma, chronic granulocytic leukemia, primary brain carcinoma, malignant melanoma, small-cell lung carcinoma, stomach carcinoma, colon carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, renal cell carcinoma, endometrial carcinoma, essential thrombocytosis, adrenal cortex carcinoma, skin cancer, and prostatic carcinoma. Furthermore, specific cellular proliferation disorders are encompassed by the present invention, such as, for example, benign prostate hyperplasia, familial adenomatosis polyposis (FAP), psoriasis, vascular smooth cell proliferation associated with atherosclerosis, pulmonary fibrosis, hyperkeloidosis, glomerulonephritis and post-surgical stenosis and restenosis.

According to the present invention an "autoimmune disorder" or "autoimmune disease" as used herein is a group of diseases or disorders arising from an pathological immune response, either humoral or cellular or both, directed against an individual's own tissues and condition resulting therefrom.

Examples of autoimmune diseases or disorders include, but are not limited to acute and chronic rheumatoid diseases such as rheumatic fever, rheumatoid arthritis, osteoarthritis, psoriatic arthritis, and ankylosing spondylitis, Sjögren's syndrome, Stevens-Johnson syndrome, acute and chronic autoimmune diseases of the skin such as urticaria, dermatomyositis, toxic epidermal necrolysis, scleroderma, multiple sclerosis, pyoderma gangrenosum, erythema nodosum, systemic lupus erythematosus (SLE), allergic conditions, such as asthma, and autoimmune gastrointestinal and endocrine disorders such as ulcerous colitis, Crohn's disease, diabetes mellitus, Hashimotos thyroiditis, autoimmune dilatative myocarditis, autoimmune vasculitis such as thrombangitis obliterans, and myositis, autoimmune anemia and autoimmune forms of myelophtisis, idiopathic thrombocytopenic purpura (ITP) and autoimmune diseases of the kidneys such as acute and chronic glomerulonephritis.

As used herein, "pharmaceutically acceptable carrier" means any of the various carriers known to those skilled in the art. The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbonyl and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

The invention therefore provides a method for orally delivering a glycosaminoglycan to a subject comprising administering to the subject a pharmaceutically effective amount of one of the above-mentioned pharmaceutical compositions.

The pharmaceutical composition(s) of the present invention is/are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

Dosage levels of approximately 0.01 mg to about 500 mg of sulfated polysaccharide per kilogram of body weight per day are useful in the treatment of the above-indicated conditions. For example, cell proliferation disorders may be effectively treated by the administration of about 0.01 to 100 mg of the compound per kilogram of body weight per day (about 0.5 mg to about 3.5 g per patient per day). The amount of active ingredient that may be combined with the carrier materials to produce a single dosage form will vary depending upon the host treated and the particular mode of administration. For example, a formulation intended for the oral administration in humans may vary from about 1 to about 95% of the total composition. Dosage unit forms will generally contain between about 1 mg to about 500 mg of active ingredient. It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy. The dosage effective amount of compounds according to the invention will vary depending upon factors including the particular compound, toxicity, and inhibitory activity, the condition treated, and whether the compound is administered alone or with other therapies. Typically a dosage effective amount will range from about 0.0001 mg/kg to 1500 mg/kg, more preferably 1 to 1000 mg/kg, more preferably from about 1 to 150 mg/kg of body weight, and most preferably about 10 to 100 mg/kg of body weight.

Animal models conducted with PPS administration have typically used between 10 and 30 mg/kg body weight PPS during treatment for enhanced allograft survival, for example in Schwartz et al (Journal of Surgical Research, Volume 86, Issue 1, September 1999, Pages 24-28).

The invention also relates also to a process or a method for the treatment of the above mentioned pathological conditions. The compounds of the present invention can be administered prophylactically or therapeutically, preferably in an amount that is effective against the mentioned disorders, to a warm-blooded animal, for example a human, requiring such treatment, the compounds preferably being used in the form of pharmaceutical compositions.

FIGURES

The invention is further described by the figures. These are not intended to limit the scope of the invention.

EXAMPLES

The invention is further described by the following examples. These are not intended to limit the scope of the invention. The experimental examples relate to qualitative and quantitative microscopic analysis of various cell types and the adherence of platelets to the surface of said cells. Various Glycosaminoglycans and their effect on platelet binding have been assessed.

The methods used in the following examples are described below. The process outlined herein for the determination of platelet interaction with cells is suitable for the examination of whether, and in which concentration, a test substance is able to prevent the platelets binding to the surface of a growing cell. Furthermore, the method can be used as a bioassay for determining the concentration of substances, which can inhibit platelet binding to cells.

Summary of the Examples

Example 1: Microscopic analysis of HeLa cells and skin fibroblasts with respect to platelet binding to the surface of cells (FIGS. 1 to 4).

Example 2: Analysis of low molecular weight (LMW) heparins with respect to inhibition of platelet binding to the surface of growing cells (FIGS. 5 to 9)

Example 3: Analysis of fondaparinux and danaparoid with respect to inhibition of platelet binding to the surface of growing cells.

Figure 10:
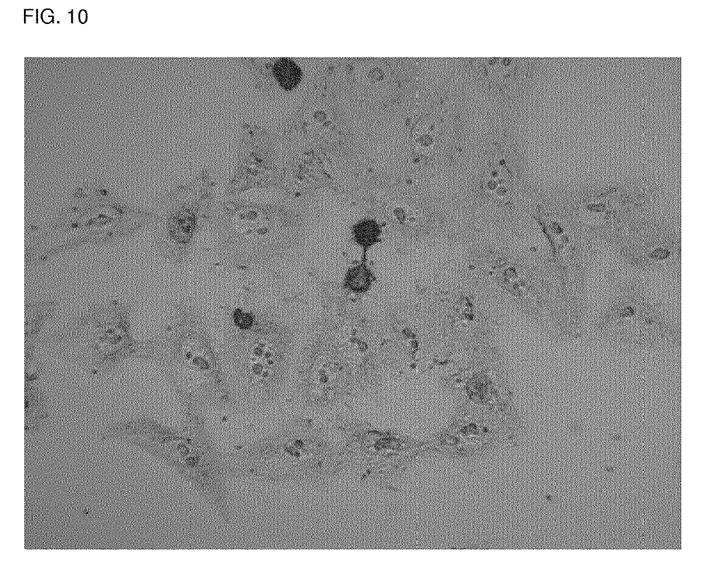
FIG. 10. HeLa cells, clone S3, treated with 0.1 ug/mL PPS. Platelets are shown as dark spots.
Figure 11:
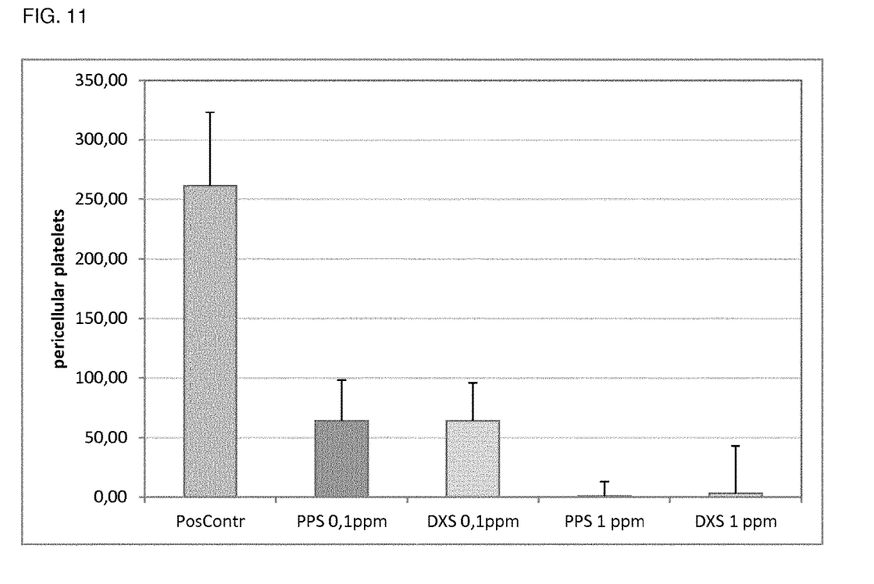
FIG. 11. Inhibition of platelet binding to growing cells by the sulfated GAGs PPS and DXS. Quantification of microscopic analysis. Error bars relate to standard deviation over experiments performed in triplicate. Inhibition of platelet binding to growing cells by the sulfated GAG's PPS and DXS amounts to roughly 75% by 0.1 ppm of PPS or DXS and to more than 95% by 1 ppm.

Example 4: Analysis of sulfated GAGs pentosan polysulfate (PPS) and dextranpolysulfate (DXS) with respect to inhibition of platelet binding to the surface of growing cells (FIGS. 10 and 11).

Figure 12:
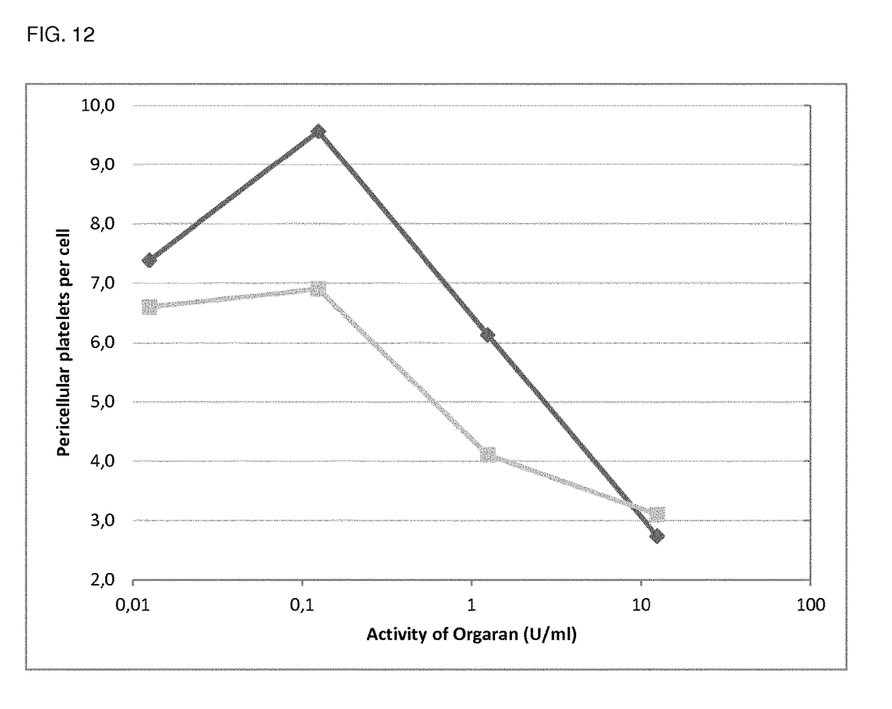
FIG. 12. Comparison between highly and lowly sulphated GAGs on platelet binding to growing cells. Danaparoid (Orgaran) (squares) exhibits an inhibitory effect on the interaction between platelets and the cell surface, although to a lower extent than the highly sulphated PPS (diamonds).

Example 5: Comparative analysis of GAGs on platelet binding between highly and lowly sulfated GAGs (FIG. 12).

Detailed Description of the Examples

Example 1

Figure 1:
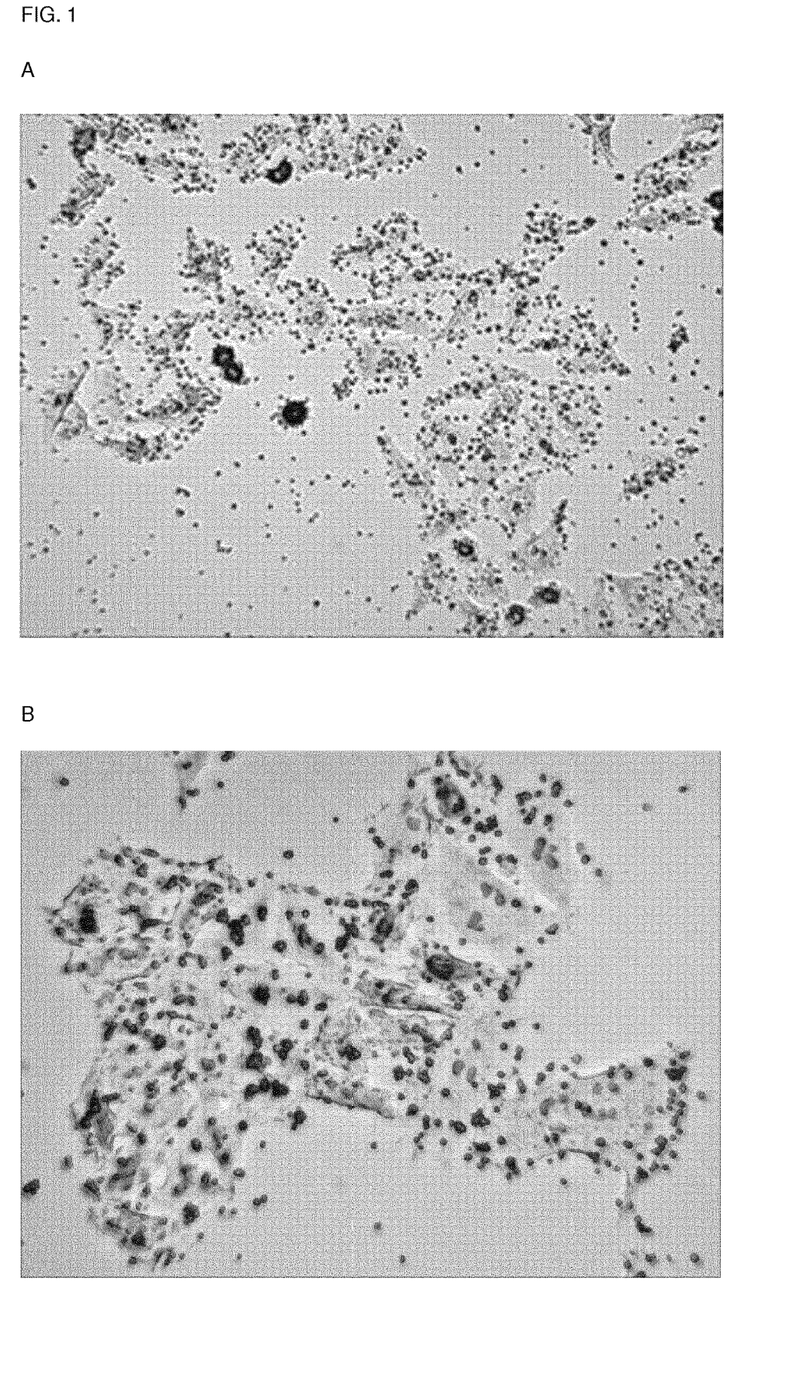
FIG. 1. Selective binding of thrombocytes to the surfaces of growing HeLa cells. (A) Culture 2 days after passage. Platelets shown as dark spots. (B) Enlarged view demonstrates cell surface interaction.

As shown in FIG. 1, it was confirmed that HeLa cells have a specific binding ability for platelets. The binding of platelets to HeLa cells was 20 to 100 times higher than that on the surface of the cell culture plates. Platelets were prepared as described below and applied to cells in culture as described.

Figure 2:
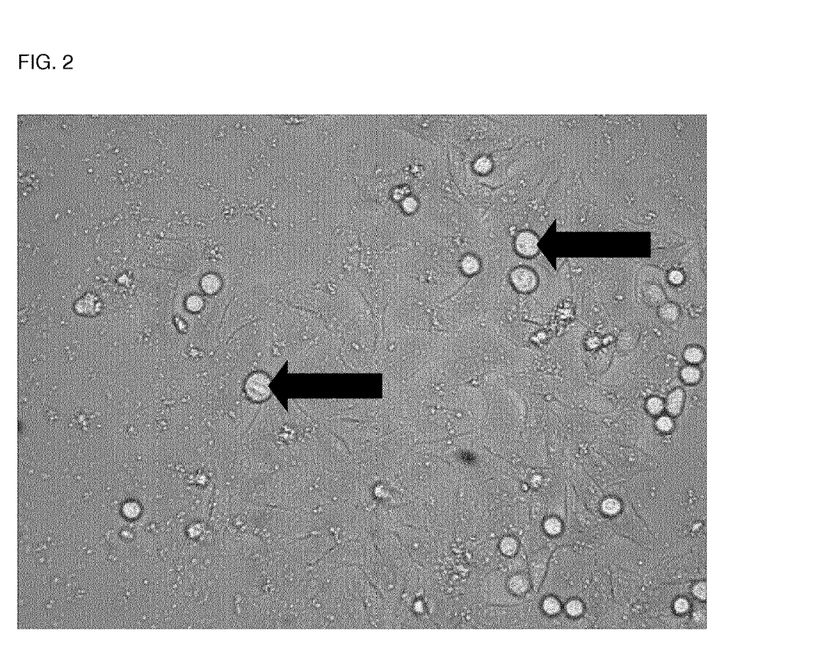
FIG. 2. HeLa growth experiment. Cell division and growth are still found after seven days in serum-free culture medium when the cells are co-incubated once a day for 30 minutes with platelets and are subsequently washed and further cultured with serum-free culture medium. Unstained, living cells, nearly confluent after 7 days in culture are shown. Arrows: metaphase of mitosis. Adherent platelets shown as light spots.

FIG. 2 demonstrates that serum free medium may be used for HeLa culture if platelets are provided to the cells for 30 minutes daily. The short duration of daily platelet contact to the cells leads to slightly reduced proliferation. This experiment shows that platelets are able to sustain proliferation of cells, substituting the serum supplement otherwise needed in vitro.

Figure 3:
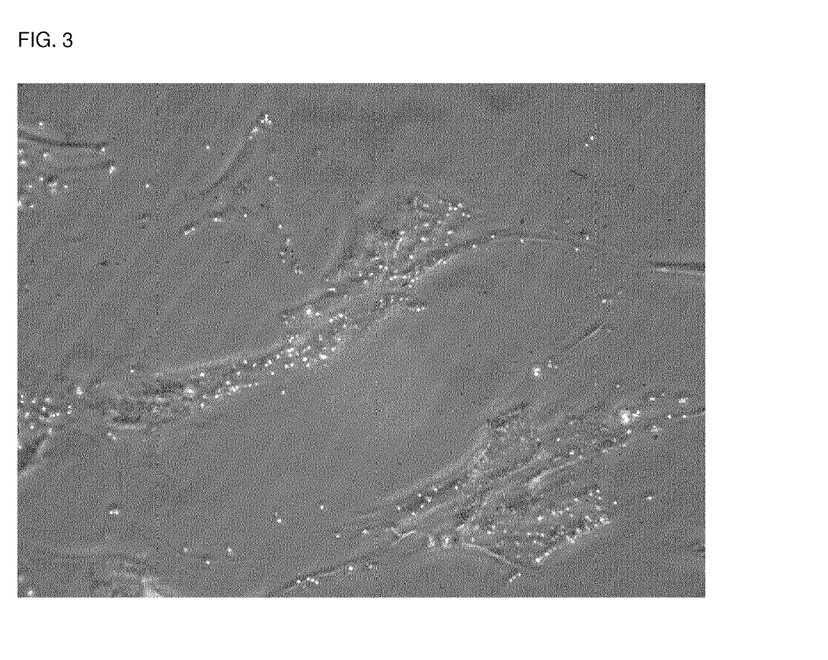
FIG. 3. Growing cells bind platelets. Here human primary skin fibroblasts in the first passage are shown. Platelets are shown as light spots.
Figure 4:
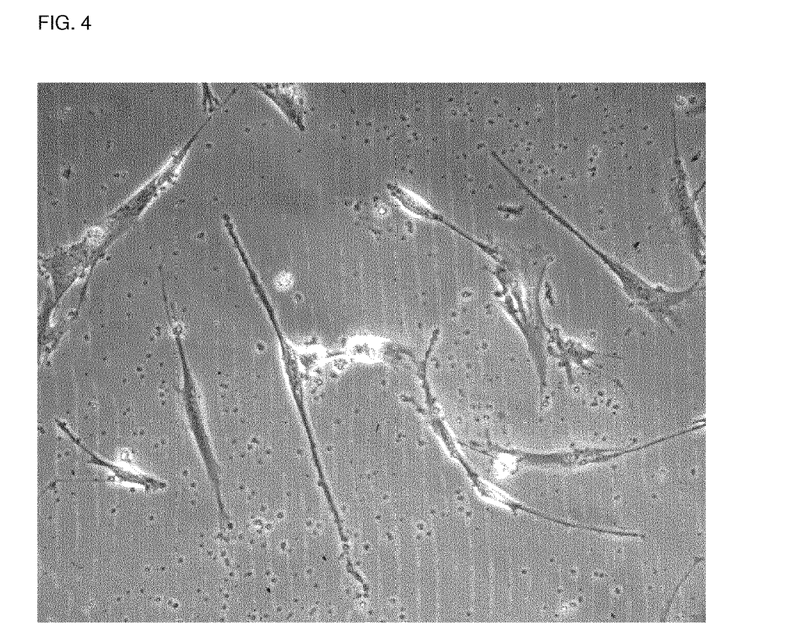
FIG. 4. Aging culture of skin fibroblasts. Poor platelet binding is shown. Platelets are shown as dark spots.
Figure 5:
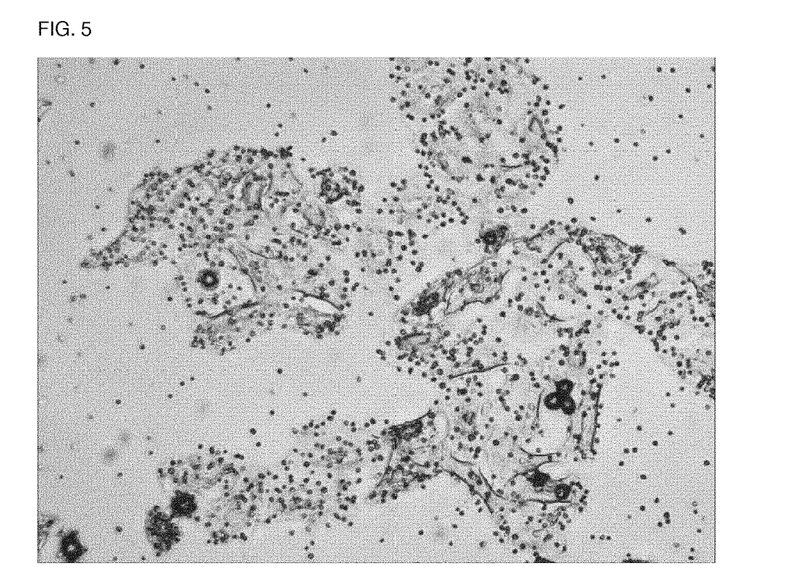
FIG. 5. Untreated HeLa cells, clone S3. Platelets are shown as dark spots.
Figure 6:
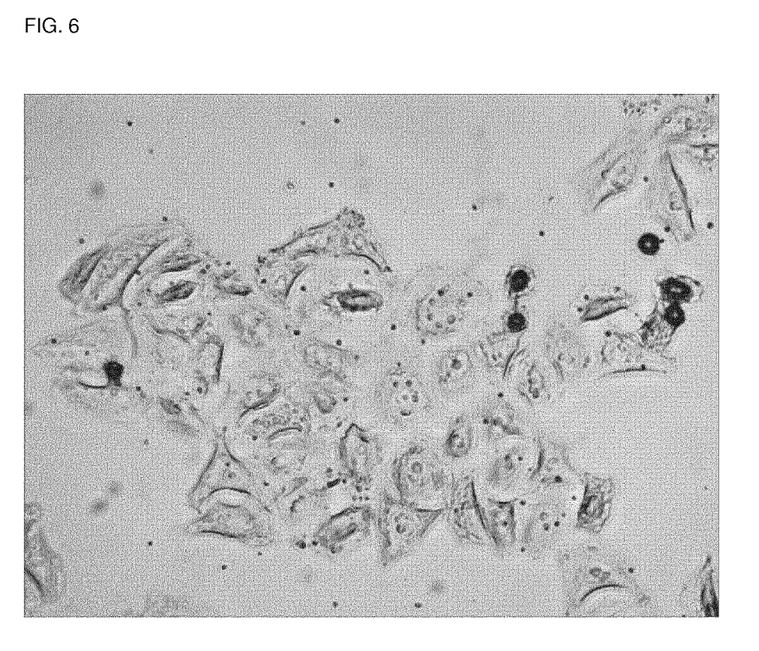
FIG. 6. HeLa cells, clone S3, treated with 1 U/mL Enoxaparin. Platelets are shown as dark spots.
Figure 7:
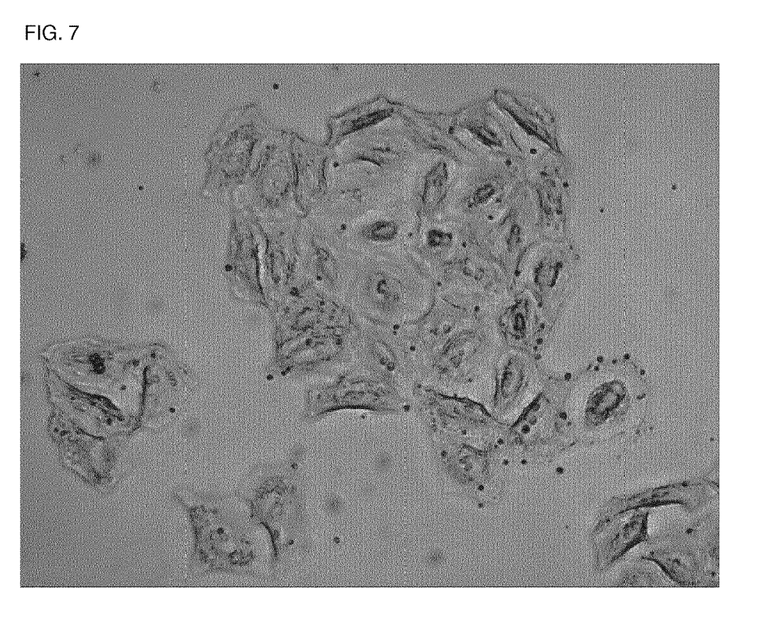
FIG. 7. HeLa cells, clone S3, treated with 1 U/mL Dalteparin. Platelets are shown as dark spots.
Figure 8:
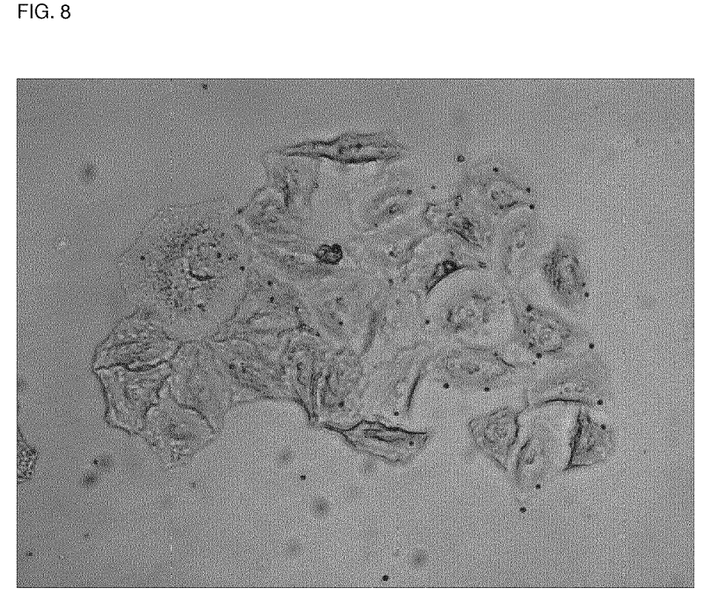
FIG. 8. HeLa cells, clone S3, treated with 1 U/mL Tinzaparin. Platelets are shown as dark spots.
Figure 9:
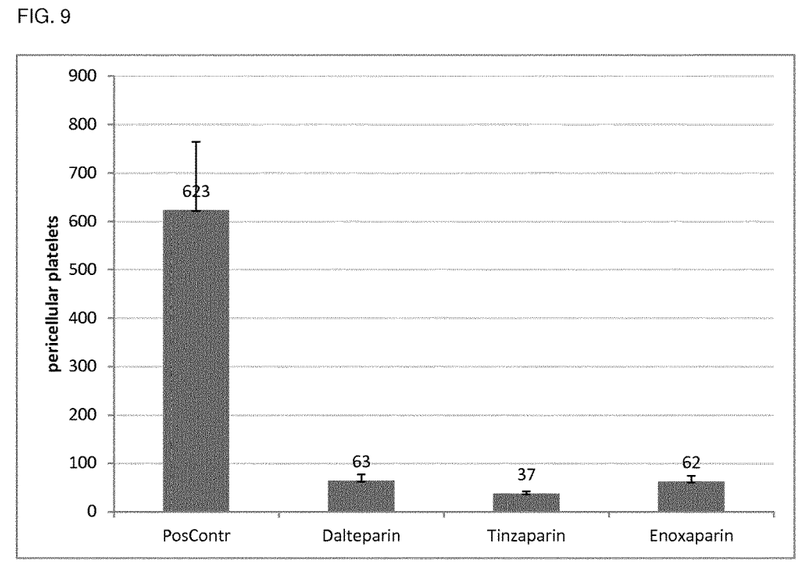
FIG. 9. LMW Heparins inhibit platelets from binding to growing cells. Quantification of microscopic analysis. The 0-value relates to cells with no addition of thrombocytes to the cell culture. The positive control shows platelet binding without addition of LMW Heparins. Error bars relate to standard deviation over experiments performed in triplicate.

FIGS. 3 and 4 demonstrate that skin fibroblasts bind platelets on their surface dependent on their growth phase. Fibroblasts that are proliferating in culture bind significantly more platelets than those in older cultures. Primary human skin fibroblasts NHDF bind platelets in the first logarithmic growth phase, similar to the examined HeLa cells, but to a somewhat lower extent than in HeLa cells. The concomitant decreased proliferation with decreased platelet binding of NHDF shows that platelets are also of importance in the proliferation of normal primary cells. The higher percentage of cells in the G0 phase is associated with down-regulation of the number of platelet receptors. This indicates that the platelet itself can initiate the transduction of proliferative stimulus. This can be a crucial phenomenon in malignant transformation. This could be similar to some cells entering the cell cycle by inducing platelet receptors, which are not always present. Platelet binding therefore leads to proliferation-inducing signal transduction.

Example 2

It could also be shown that enoxaparin, dalteparin and tinzaparin, corresponding to 0.1 U/mL, almost completely inhibited the binding of platelets to the HeLa cells (FIGS. 5 to 9). Even in a concentration of 0.01 U/mL a significant reduction of platelet binding to the cells took place.

Example 3

However, fondaparinux, a synthetic pentasaccharide corresponding to the five monomeric sugar units that can be isolated after either chemical or enzymatic cleavage of the polymeric glycosaminoglycan heparin, was unable to significantly inhibit platelet binding to HeLa cells. Furthermore, treatment with danaparoid, an anticoagulant chemically distinct from heparin (also known as Orgaran), showed a significantly lower effect on inhibiting the interaction between platelets and the cell surface.

When danaparoid is applied at 1.25 U/mL, which is about 5 times the upper limit of the therapeutic range, no significant difference is found between the control measurements (15.9+/−7.7 platelets/cell) and the danaparoid treatment (13.2 platelets/cell).

Heparins, and some other anticoagulants, have the disadvantage that they have an overly strong anticoagulant effect and can cause serious bleeding complications, which are mainly attributed to the aforementioned inhibition of coagulation factor Xa. The most important factor in the anticoagulant effect of heparin is a sulfated pentasaccharide, which inactivates the coagulation factor Xa. However, the aforementioned pentasaccharide does not inhibit platelet binding to growing cells.

Interestingly, danaparoid exhibits a lower degree of sulfation (typically 0.4 to 0.6) in comparison to Heparin (typically 1 to 2). Also significantly less effective as inhibitors of platelet binding were other low sulfated chondroitin sulfate GAGs, such as dermatan sulfate and heparan sulfate.

Example 4

Pentosan polysulfate (PPS) is a vegetable product and is manufactured as the sodium salt or calcium salt. PPS typically has less than 1/10 of the anticoagulant activity of heparin and has been used for the treatment of interstitial cystitis and used in veterinary medicine for joint disease, in particular for forms of arthritis. Dextran polysulfate (DXS) is also used to treat joint pain, usually in combination with other substances.

As shown in FIGS. 10 and 11, both PPS and DXS exhibit a reproducible inhibition of the physical interaction between platelets and the surface of proliferating cells.

Example 5

As demonstrated in FIG. 12, treatment of the cell cultures with danaparoid in direct comparison to PPS shows the distinct difference between these two molecules with respect to their disruption of platelet binding to the surfaces of cells.
Methods:

The process for evaluating the platelet binding of growing cells involves the isolation of platelets from peripheral blood with two subsequent washes and cell sedimentation. These washes include a partial activation of the platelets, which is relevant for their interaction with Heparin. The incubation with the cells under investigation takes place under conditions in which full activation of platelets is approached, which would lead to lumps forming in the platelets. This would hinder analysis. Therefore, a low concentration of EDTA is added to the assay. The quantification of platelets and the calculation of the surface portions of cells and background is carried out using appropriate software, namely by macros in the open source program ImageJ.
Platelet Isolation Procedure:

Various methods are available for platelet isolation. The following method is preferred.

Experimentation by the inventor has shown that the activation of platelets, which ultimately leads to a viscous metamorphosis of the platelets as a result, can take place in two stages. The first stage involves no significant morphological change in the platelets, but does lead to a slight change in the appearance of their outer surface. These platelets are referred to as "partially activated platelets". This change is important for the adhesion test as described herein, in order to optimize the ability to bind receptors on the cell surface.

First centrifuge blood samples for 7 minutes at 190×G in a centrifuge without a brake. This separates plasma and erythrocytes. During centrifugation a 10 ml tube with 1 ml of PBS-EDTA is prepared. The platelet-rich plasma is pipetted into the prepared tubes. An EDTA-PBS refill is carried out if necessary. The final mixture should be 1:1 EDTA-PBS and plasma.

The platelet-containing plasma is centrifuged to separate the platelets from the plasma. The centrifugation is carried out at 265-275×G. The duration depends on the size of the tube used (for example 16 mm diameter×100 mm length; centrifugation for 15 minutes at 270×G).

The resulting sediment is quite loose. The supernatant is discarded. The platelet sediment, with very little buffer mixture, is allowed to stand for 3 minutes and is loosened by gentle shaking. The platelets are resuspended in the following buffer mixture:

2 mL of 1:1 v/v Hank's Balanced Salt Solution (HBSS) with Ca and Mg, and a buffer solution without Ca and Mg. The latter buffer solution can either be HBSS without Ca and Mg or for example Dulbecco's Phosphate Buffered Saline Solution (PBS), which has been produced without Ca and Mg. The aforementioned buffer mixture is treated with 0.02% EDTA.

The viscous metamorphosis of platelets is dependent on Ca and Mg. The tendency of the platelets to undergo this change should be reduced for the trial. However, when maintained in tissue culture, cells cannot tolerate a one-hour incubation in a completely Ca and Mg-free environment. The aforementioned mixture is sufficient to buffer a conditioning of platelets and contains at the same time sufficient Ca and Mg for metabolic function of the cells in culture.

The platelet suspension has not yet obtained the optimal properties for the adhesion test. They are therefore conditioned by centrifugation for 15 minutes at 265-275 x G. The buffer is discarded and the now noticeably firmer sediment is mixed with 2 mL buffer mixture and allowed to stand for 3 minutes, then loosened by gentle shaking. The centrifugation is then repeated and the platelet count is determined.

Adhesion Experiment (Platelet Binding to Cell Surface):

Virus and mycoplasma free HeLa cells, clone S3, and human skin fibroblasts (NHDF) were purchased from Promo Cell, Heidelberg. Their human origin was confirmed by STR-Analysis. HeLa cells were maintained in Eagles MEM with 10% fetal calf serum. The NHDF were also maintained with 10% fetal calf serum in RPMI 1640. The passaging was performed by trypsin-EDTA treatment. The cell lines were maintained in either 25 ml bottles or in 3 cm plates.

The cells used for the experiment are cultured for 2 or 3 days in standard plates. At the start of the experiment about ⅓ of the plate surface should be covered with cells. The culture plates are subsequently washed with the buffer mixture described above and filled with further buffer mixture. For example, 30 mm culture dishes are filled with 2 ml 37° C. pre-warmed buffer mixture and $3 \times 10^7$ platelets obtained from the above-mentioned suspension.

The platelet-treated plates are incubated at 37° C. for 60 minutes. In this incubation, the pretreated platelets adhere to proliferating cells. However, cells of G0-phase bind little or none of the pre-treated platelets. This stage of incubation is when the substance to be tested is added to the cell culture buffer, in order to detect whether an effect on platelet binding is observed.

After the one hour incubation, the plates are washed at room temperature with the above mentioned buffer mixture until no free water floating platelets (generally 2 to 4 washes) are present and immediately fixed with glutaraldehyde (1% v/v in H2O).

The evaluation is carried out photographically. For this purpose, the image analysis program ImageJ is applied. The number of cell-bound platelets in relation to the recorded cell number of cells is determined. Additionally, the number of cell-bound platelets in relation to the cell-covered area may be determined.

Photographic Documentation:

Images are produced after the fixation in triplicate per plate. Phase contrast or brightfield 25×, 16× or 10× objectives are used. Image analysis is carried out according to SOP IJ. The open source program ImageJ may be used to for differential image subtraction and mask optimization. Subsequently, platelet number, cell number and proportional cell surface are determined by other IJ components.

Cell Culture Experiments for Testing Inhibition of Cell Proliferation:

Additional experimentation shows that administration of sulfated polysaccharides, in particular glycosaminoglycans, leads directly to inhibition of cell proliferation under conditions that mimic the in vivo requirements for cell growth that is dependent on platelet-cell surface interactions. In order to interrogate the effectiveness of PPS and DXS with respect to the inhibition of cell growth, the following experiment may be carried out.

Experiment duration: 5 days; Culture medium: Eagle's MEM without serum addition.

Test approach: PPS or DXS in 1.0, 0.1 µg/mL, and control (0 µg/mL final concentration).

HeLa cells are cultured from stocks: $10^4$ cells/25 cm² flask, cell numbers are counted in a Fuchs-Rosenthal chamber. Platelets are prepared as described above.

Platelets and HeLa cells, or other tumor cell lines, either with or without inhibitor, are co-incubated for 30 minutes once every day, for 1 to 4 days. After co-incubation the cells are washed as described above and then allowed to rest under standard culture conditions. Typically $90 \times 10^6$ platelets are incubated per well per day.

On day 5, cells are washed with HBSS, photographed, trypsinized and the cell number counted as described above. This experimental approach shows that the number of cells, which typically increases via proliferation due to the daily 30 minute incubation with thrombocytes, increases to a reduced extent when either DXS or PPS is co-incubated with the platelets during the 30 minute incubation.

The invention claimed is:

1. A method of treating cancer in a subject in need thereof comprising administering a pharmaceutical composition comprising a soluble sulfated polysaccharide to said subject, wherein said soluble sulfated polysaccharide does not comprise the terminal pentasaccharide of Heparin and has a degree of sulfation of greater than or equal to 1, and wherein proliferation of cancerous cells in the subject is reduced by said soluble sulfated polysaccharide inhibiting a physical interaction between cancer cell surfaces and platelets.

2. The method according to claim 1, wherein said subject is a human.

3. The method according to claim 1, wherein the degree of sulfation of said polysaccharide is >1.2.

4. The method according to claim 1, wherein the degree of sulfation of said polysaccharide is >1.4.

5. The method according to claim 1, wherein the soluble sulfated polysaccharide exhibits an average molecular weight of about 5000 to about 12000 daltons.

6. The method according to claim 1, wherein the soluble sulfated polysaccharide is pentosan polysulfate (PPS).

7. The method according to claim 1, wherein the soluble sulfated polysaccharide is dextran sulfate (DXS).

8. The method according to claim 1, wherein said soluble sulfated polysaccharide is a sulfated alginate.

9. The method according to claim 1, wherein said soluble sulfated polysaccharide is a sulfated fucoidan.

10. The method according to claim 1, wherein said soluble sulfated polysaccharide is locally administered in proximity to a tumor.

* * * * *